United States Patent
Neu et al.

(10) Patent No.: US 11,274,087 B2
(45) Date of Patent: Mar. 15, 2022

(54) INDUSTRIAL PROCESS FOR THE PREPARATION OF CARIPRAZINE

(71) Applicant: Richter Gedeon Nyrt., Budapest (HU)

(72) Inventors: József Neu, Budapest (HU); Sándor Garadnay, Budapest (HU); Tamás Szabó, Dorog (HU)

(73) Assignee: Richter Gedeon Nyrt.

( * ) Notice: Subject to any disclaimer, the term of this patent is extended or adjusted under 35 U.S.C. 154(b) by 210 days.

(21) Appl. No.: 16/316,312

(22) PCT Filed: Jul. 7, 2017

(86) PCT No.: PCT/IB2017/054094
§ 371 (c)(1),
(2) Date: Jan. 8, 2019

(87) PCT Pub. No.: WO2018/007986
PCT Pub. Date: Jan. 11, 2018

(65) Prior Publication Data
US 2021/0276965 A1    Sep. 9, 2021

(30) Foreign Application Priority Data
Jul. 8, 2016 (HU) ..................... 1600420

(51) Int. Cl.
*C07D 295/135* (2006.01)
*C07C 229/48* (2006.01)

(52) U.S. Cl.
CPC ........ *C07D 295/135* (2013.01); *C07C 229/48* (2013.01)

(58) Field of Classification Search
CPC .................... C07D 295/135; C07C 229/48
See application file for complete search history.

(56) References Cited

U.S. PATENT DOCUMENTS

| | | | |
|---|---|---|---|
| 4,666,911 A | 5/1987 | Fujimura et al. |
| 4,943,632 A | 7/1990 | Robinson |
| 4,957,921 A | 9/1990 | Caprathe et al. |
| 5,384,323 A | 1/1995 | Bolz |
| 5,807,575 A | 9/1998 | Dumoulin |
| 5,846,514 A | 12/1998 | Foster et al. |
| 5,910,319 A | 6/1999 | Anderson et al. |
| 6,334,997 B1 | 1/2002 | Foster et al. |
| 6,395,739 B1 | 5/2002 | Sato et al. |
| 6,489,341 B1 | 12/2002 | Jerussi |
| 6,528,529 B1 | 3/2003 | Brann et al. |
| 6,566,550 B2 | 5/2003 | Lowe, III |
| 6,667,060 B1 | 12/2003 | Vandecruys |
| 6,919,342 B2 | 7/2005 | Haupt |
| 7,122,576 B2 | 10/2006 | Plata-Salaman et al. |
| 7,737,142 B2 | 6/2010 | Csongor et al. |
| 7,829,569 B2 | 11/2010 | Liao et al. |
| 7,875,610 B2 | 1/2011 | Szalai et al. |
| 7,943,621 B2 | 5/2011 | Czibula et al. |
| 7,981,897 B2 | 7/2011 | Bathe et al. |
| 8,569,496 B2 | 10/2013 | Czibula et al. |
| 8,569,497 B2 | 10/2013 | Czibula et al. |
| 8,569,498 B2 | 10/2013 | Czibula et al. |
| 8,765,765 B2 | 7/2014 | Csongor et al. |
| 8,802,672 B2 | 8/2014 | Szalai et al. |
| 8,802,888 B2 | 8/2014 | Mathe et al. |
| 8,846,100 B2 | 9/2014 | Shojaei |
| 9,056,845 B2 | 2/2015 | Sarkar et al. |
| 9,056,846 B2 | 2/2015 | Sarkar et al. |
| RE47,333 E | 4/2019 | Sarkar et al. |
| RE47,350 E | 4/2019 | Sarkar et al. |
| 2001/0009912 A1 | 7/2001 | Tsaklakidis et al. |
| 2003/0144285 A1 | 7/2003 | Brann et al. |
| 2004/0259882 A1 | 12/2004 | Haupt et al. |
| 2005/0107397 A1 | 5/2005 | Galambos et al. |
| 2006/0229297 A1 | 10/2006 | Csongor et al. |

(Continued)

FOREIGN PATENT DOCUMENTS

| | | |
|---|---|---|
| CN | 105218484 | 1/2016 |
| CN | 105330616 | 2/2016 |
| EP | 0224751 | 10/1987 |
| EP | 0453574 | 10/1991 |
| EP | 0431580 | 3/1995 |
| EP | 2251011 | 11/2010 |
| EP | 16165247 | 10/2017 |
| JP | 01-199977 | 8/1989 |
| JP | 01-308284 | 12/1989 |
| JP | 04-275280 | 9/1992 |
| JP | 05-032586 | 2/1993 |
| JP | 05-310745 | 11/1993 |
| KR | 2005/0043131 | 5/2005 |

(Continued)

OTHER PUBLICATIONS

[No Author Listed], "The ICD-10 classification of mental and behavioral disorders : clinical descriptions and diagnostic guidelines," Geneva; World Health Organization, 1992, 263 pages.
Abraham, Ed., "History of Quantitative Structure-Activity Relationships," Burger's Medicinal Chemistry and Drug Discovery, 6th edition, vol. 1, pp. 1-48, (Jan. 2003).

(Continued)

*Primary Examiner* — Rebecca L Anderson
(74) *Attorney, Agent, or Firm* — Fish & Richardson P.C.

(57) ABSTRACT

In the process of the present invention, cariprazine is prepared by converting (trans-4-amino-cyclohexyl)-acetic acid ethyl ester hydrochloride to trans-4-aminocyclohexyl) acetic acid or its hydrochloride by hydrolysis, from the obtained product with addition of dimethylcarbamoyl derivative as a suitable reagent (trans-4-{[(dimethylamino)carbonyl]amino}cyclohexyl) acetic acid is formed, then the obtained compound is linked to 1-{2,3-dichlorophenyl)~piperazine in the presence of carboxylic acid activating coupling reagent, and so 1,1-dimethyl-3-[trans-4-(2-oxo-2-(4-(2,3-dichloro-phenyl)piperazin-1-yl-ethyl)cyclohexyl] urea is formed, which is converted to cariprazine borane adduct of formula (2) in the presence of reducing agent, and finally the product itself is eliminated directly or is obtained from its salt by a known method. The invention also relates to a group of intermediate compounds that are formed and/or used in the process according to the present invention.

16 Claims, No Drawings

(56) References Cited

U.S. PATENT DOCUMENTS

| | | |
|---|---|---|
| 2007/0099931 A1 | 5/2007 | Ghosh et al. |
| 2007/0244093 A1 | 10/2007 | Boehm et al. |
| 2007/0259885 A1 | 11/2007 | Bathe et al. |
| 2009/0023750 A1 | 1/2009 | Czibula et al. |
| 2009/0036468 A1 | 2/2009 | Samoriski et al. |
| 2010/0016334 A1 | 1/2010 | Sarkar |
| 2010/0137335 A1 | 6/2010 | Csongor et al. |
| 2010/0197666 A1 | 8/2010 | Laszlovsky et al. |
| 2010/0197704 A1 | 8/2010 | Laszlovsky et al. |
| 2010/0256145 A1 | 10/2010 | Bak-Jensen et al. |
| 2011/0059980 A1 | 3/2011 | Oobayashi |
| 2011/0269959 A1 | 11/2011 | Csongor et al. |
| 2011/0275804 A1 | 11/2011 | Czibula et al. |
| 2011/0275816 A1 | 11/2011 | Czibula et al. |
| 2011/0288329 A1 | 11/2011 | Mathe et al. |
| 2013/0040966 A1 | 2/2013 | Sarkar |
| 2015/0306094 A1 | 10/2015 | Fitter |
| 2019/0117647 A1 | 4/2019 | Imada et al. |
| 2020/0222391 A1 | 7/2020 | Konta et al. |
| 2020/0323842 A1 | 10/2020 | Roman et al. |

FOREIGN PATENT DOCUMENTS

| | | |
|---|---|---|
| WO | WO 1991/07411 | 5/1991 |
| WO | WO 1997/011070 | 3/1997 |
| WO | WO 1999/050247 | 10/1999 |
| WO | WO 1999/067206 | 12/1999 |
| WO | WO 2001/005763 | 1/2001 |
| WO | WO 2003/029233 | 4/2003 |
| WO | WO 2003/064393 | 8/2003 |
| WO | WO 2005/012266 | 2/2005 |
| WO | WO 2006/034774 | 4/2006 |
| WO | WO2006/44524 | 4/2006 |
| WO | WO 2006/082456 | 8/2006 |
| WO | WO 2007/033191 | 3/2007 |
| WO | WO 2008/038003 | 4/2008 |
| WO | WO 2008/139235 | 11/2008 |
| WO | WO 2008/141135 | 11/2008 |
| WO | WO 2008/142461 | 11/2008 |
| WO | WO 2008/142462 | 11/2008 |
| WO | WO 2009/020897 | 2/2009 |
| WO | WO 2009/104739 | 8/2009 |
| WO | WO 2010/009309 | 1/2010 |
| WO | WO 2010/070368 | 6/2010 |
| WO | WO2010/070369 | 6/2010 |
| WO | WO 2010/126527 | 11/2010 |
| WO | WO 2011/060363 | 5/2011 |
| WO | WO 2013/169101 | 11/2013 |
| WO | WO 2014/031162 | 2/2014 |
| WO | WO 2014/083522 | 6/2014 |
| WO | WO2015/056164 | 4/2015 |
| WO | WO 2015/086836 | 6/2015 |

OTHER PUBLICATIONS

Abstracts of Papers, 234th ACS National Meeting, Boston, MA, United States, Aug. 19-23, 2007, MEOI-383, Jul. 25, 2007, 268 pages.
Aiken, "Pramipexole in psychiatry: A systematic review of the literature," J. Clin Psychiatry., 68(8):1230-1236, (2007).
Alphs et al., "Asenapine in the Treatment of Negative Symptoms of Schizophrenia: Clinical Trial Design and Rationale Psychopharmacology Bulletin," 2007, 40(2):41-53.
Archer and Kostrzewa, "Neuroteratology and Animal Modeling of Brain Disorders," Neurotoxin Modeling of Brain Disorders—Lifelong Outcomes in Behavioral Teratology, 2015, pp. 1-40.
Artursson et al., "Correlation between oral drug absorption in humans and apparent drug permeability coefficients in human intestinal epithelial (Caco-2) cells," Biochem. Biophys. Res. Comm., 1991, 175(3):880-885.
Auclair et al., "P.3.c. Psychotic disorders and treatment—Treatment (basic)" World Congress of The International College of Neuropsychopharmacology, 2014, 1 page.

Baldessarini and Tarazi, "Pharmacotherapy of Psychosis and Mania," Brunton et al. (eds.), Goodman and Gilman's The Pharmacological Basis of Therapeutics, 11th Edition, McGraw Hill, Chapter 18, pp. 461-500, (2005).
Bambini-Junior et al., "Animal model of autism induced by prenatal exposure to valproate: behavioral changes and liver parameters," Brain Res., Aug. 2011, 1408:8-16.
Barnes et al., "Evidence-based guidelines for the pharmacological treatment of schizophrenia: recommendations from the British Association for Psychopharmacology," J Psychopharmacol., 25(5):567-620, (Epub Feb. 3, 2011).
Belliotti et al., "Novel Cyclohexyl Amides as Potent and Selective 0 3 Dopamine Receptor Liqands," Bioorq. Med. Chem. Lett., 1997, 7(18):2403-2408.
Berge et al., "Pharmaceutical salts," Journal of Pharmaceutical Sciences, 66(1):1-19 (1977).
Bezard et al., "Attenuation of levodopa-induced dyskinesia by normalizing dopamine D3 receptor function," Nat. Med., 9(6):762-767, (2003).
Brugha et al., "Epidemiology of autism spectrum disorders in adults in the community in England," Arch. Gen. Psychiatry., May 2011, 68(5):459-65.
Buchanan et al,"Asenapine Versus Olanzapine in People With Persistent Negative Symptoms of Schizophrenia," Journal of Clinical Psychopharmacology, Feb. 2012, 32:1:36-45.
Carpenter et al., "Treatment of negative symptoms," Schizophr Bull., 11(3):440-452, 1985.
CDC "Prevalence of Autism Spectrum Disorder Among Children Aged 8 Years—Autism and Developmental Disabilities Monitoring Network," Morbidity and Mortality Weekly Report Surveillance Summaries, 2018, 67(6):1-23.
Chadman, "Fluoxetine but not risperidone increases sociability in the BTBR mouse model of autism," Pharmacol. Biochem. Behav., Jan. 2011, 97(3):586-94.
Clinicaltrials.gov, NCT02165098, "Cariprazine: Comparison of Slow- and Immediate-Release Forms," dated Mar. 24, 2016, 6 pages.
Christensen et al., "Prenatal valproate exposure and risk of autism spectrum disorders and childhood autism," Jama, Apr. 2013, 309(16):1696-703.
Creese et al., "Species variation in dopamine receptor binding," Eur. J. Pharmacol., 60:55-66, (1979).
de Berardis, et al., "The novel antipsychotic cariprazine (RGH-188): state-of-the-art in the treatment of psychiatric disorders," Current Pharmaceutical Design, 2016, 22(33):5044-5162.
Damasio, "Alzheimer's Disease and Related Dementias," Cecil Textbook of Medicine, 20th Edition, vol. 2, pp. 1992-1996, (1996).
Deshpande et al., "Design and evaluation of oral bioadhesive controlled release formulations of miglitol, intended for prolonged inhibition of intestinal α-glucosidases and enhancement of plasma glucagon like peptide-1 levels," International Journal of Pharmaceutics, 2009, 380(1-2)16-24.
Dean, [Editor], "Recent Advances in the Synthesis and Applications of Radiolabeled Compounds for Drug Discovery and Development," Curr., Pharm. Des., vol. 6, No. 10, [Table of Contents] CAN 133:68895 AN 2000:473538 CAPLUS; 3 pages, (2000).
Di Chiara, "Drug addiction as dopamine-dependent associative learning disorder," Eur. J. Pharmacol., 375: 13-30, (1999).
Eli Lilly and Company, "Zyprexa Olanzapine Tablets . . . . " MedWatch Safety Alerts for Human Medical Products, FDA [online]. Retrieved from the Internet:<URL: http://www.fda.gov/medwatch/safety/2006/Aug_PIs/Zyprexa_PI.pdf>, 31 pages, (2004).
Elsabbagh et al., "Global prevalence of autism and other pervasive developmental disorders," Autism research, Jun. 2012, 5(3):160-179.
EP Search Report in European Appln. No. PCT/HU2009/000107, dated May 27, 2010, dated May 27, 2010, 3 pages.
Evans, "Synthesis of radiolabeled compounds," J. Radioanal. Chem., 64(1-2):9-32, (1981).
FDA guidelines, "Dissolution Testing of Immediate Release Solid Oral Dosage Forms," dated Aug. 1997, Section IV-A, 5 pages.
FDA guidelines, "Extended Release Oral Dosage Forms: Development, Evaluation and Application of In Vitro/In Vivo Correlation", Food and Drug Administration, CDER, Sep. 1997, p. 17.

(56) References Cited

OTHER PUBLICATIONS

FDA guidelines, "Q3B(R2) Impurities in New Drug Products," Revision 2, Jul. 2006, 18 pages.
Gandal et al., "Validating γ oscillations and delayed auditory responses as translational biomarkers of autism," Biological psychiatiy, Dec. 2010, 68(12):1100-1106.
Glase et al., "4-bromo-1-methoxy-N-[2-(4-aryl-1-piperazinyl)ethyl]-2-naphthalenecarboxamides: Selective dopamine D3 receptor partial agonists," Bioorganic & Medicinal Chemistry Letters, 6(12):1361-1366, (1996).
Grabovac et al., "Comparison of the mucoadhesive properties of various polymers," Advanced Drug Delivery Reviews, 2005, 57(11):1713-1723.
Goodwin et al., "Medical Treatment of Acute Bipolar Depression," Manic-Depressive Illness, New York: Oxford University Press, pp. 639-651, (1990).
Graff-Guerrero et al., "The effect of antipsychotics on the high-affinity state of D2 and D3 receptors: a positron emission tomography study With [11C]-(+)-PHNO," Arch. Gen. Psychiatry, Jun. 2009, 66(6):606-615.
Greengrass et al., "Binding characteristics of 3H-prazosin to rat brain alpha-adrenergic receptors," Eur. J. Pharmacol., 55(3):323-326, (1979).
Grunder et al., "Brain and plasma pharmacokinetics of aripiprazole in patients with schizophrenia: an [18F] fallypride PET study," Am. J. Psychiatry, Aug. 2008, 165(8):988-995.
Guérémy et al., "2-Amino-6-chloro-4-(N-methylpiperazino)pyrimidines, inhibitors of spiroperidol binding," J. Med. Chem., 1982, 25(12):1459-1465.
Gurevich et al., "Mesolimbic dopamine D3 receptors and use of antipsychotics in patients with schizophrenia. A postmortem study." Arch Gen Psychiatry., 54(3):225-232, (1997).
Gurevich et al., "Distribution of dopamine D3 receptor expressing neurons in the human forebrain: comparison with D2 receptor expressing neurons," Neuropsychopharmacology, 20(1):60-80, (Jan. 1999).
Guy et al., ECDEU Assessment Manual for Psychopharmacology. Rockville, Md: US Department of Health, Education, and Welfare, pp. 218-222, Publication ADM 76-338, (1976).
Gyertyan et al., Effects of RGH-237 [N-{4-[4-(3-Aminocarbonyl-phenyl)-piperazin-1-yl]-butyl}-4-bromo-benzamide], an Orally Active, Selective Dopamine D3 Receptor Partial Agonist in Animal Models of Cocaine Abuse, Journal of Pharmacology and Experimental Therapeutics., Mar. 2007, 320(3):1268-78.
Gyertyan et al., "RGH-790, A selective dopamine D3/D2 receptor partial agonist with cognitive enhancer properties," World Psychiatric Association International Conference, Prague, 1 page [poster], (Oct. 17-21, 2012).
Gyertyán et al., "Subnanomolar dopamine D3 receptor antagonism coupled to moderate D2 affinity results in favourable antipsychotic-like activity: Behavioral Data," Int. J. Neuropsychopharmacol., 5 Suppl. 1:S174, Abstract No. P.3.W.071, (2002).
Gyertyan et al., "Effects of dopamine $D_3$ receptor antagonists on spontaneous and agonist-reduced motor activity in NMRI mice and Wistar rats: comparative study with nafadotride, U 99194A and SB 277011," Behavioural Pharmacology, 15(4):253-262, (2004).
Gyertyán et al., "The selective dopamine D3 receptor antagonists, Sb 277011-A and S 33084 block haloperidol-induced catalepsy in rats," Eur. J. Pharmacol., 572:171-174, (2007).
Han et al., "Advances in Characterization of Pharmaceutical Hydrates," Trends in Bio/Pharmaceutical Industry, 2006, 2(3):25-29.
Hara et al., "Risperidone and aripiprazole alleviate prenatal valproic acid-induced abnormalities in behaviors and dendritic spine density in mice," Psychopharmacology (Berl), Nov. 2017, 234(21):3217-3228.
Heidbreder et al., "The role of central dopamine D3 receptors in drug addiction: a review of pharmacological evidence," Brain Res. Rev., 49:77-105, (2005).

Heusler et al., "In vitro profile of the new antipsychotic, F17464, at recombinant human neurotransmitter receptors," Eur. Neuropsychopharm. 2016, 26(S2):S490-S491.
Ichikawa et al., "Aripiprazole in the Treatment of Irritability in Children and Adolescents with Autism Spectrum Disorder in Japan: A Randomized, Double-blind, Placebo-controlled Study," Child Psychiatiy Hum. Dev., Oct. 2017, 48(5):796-806.
Janssen, "Risperdal Consta (risperidone) Long-Acting Injection," MedWatch Safety Alerts for Human Medical Products, FDA [online] Retrieved from the Internet:<URL: http://www.fda.gov/medwatch/safety/2006/Sep_PIs/RisperdalConsta_PI.pdf>. 39 pages (2006).
Joyce, "Dopamine D3 receptor as a therapeutic target for antipsychotic and antiparkinsonian drugs," Pharmacol Ther., 90:231-259, (2001).
Kabalka and Varma, "The synthesis of radiolabeled compounds via organometallic intermediates," Tetrahedron, 45(21):6601-6621, (1989).
Kay et al., "The positive and negative syndrome scale (PANSS) for schizophrenia," Schizophr. Bull., 13:261-276, (1987).
Keck, "The management of acute mania," British Medical Journal, 327(7422):1002-1003, (2003).
Keith, "Advances in psychotropic formulations," Prog Neuro-Psychopharmacol Biol Psychiatry., Aug. 30, 2006, 30(6):996-1008.
Kelley et al., "Empirical validation of primary negative symptoms: independence from effects of medication and psychosis," Am J Psychiatry., 156:406-411, 1996.
King and Schwartz, "Oral solid dosage forms," Remington's Pharmaceutical Sciences, Gennaro, A., Ed., 17th Edition, Mack Publishing Company, Easton PA, Chapter 90, pp. 1603-1632, (1985).
Kiss et al., "Cariprazine (RGH-188), a dopamine D(3) receptor-preferring, D(3)/D(2) dopamine receptor antagonist-partial agonist antipsychotic candidate: in vitro and neurochemical profile," J. Pharmacol. Exp. Ther., Apr. 2010, 333(1):328-40.
Krause et al., "Antipsychotic drugs for patients with schizophrenia and predominant or prominent negative symptoms: a systematic review and metaanalysis," European Archives of Psychiatry and Clinical Neuroscience, Oct. 2018, 268(7):625-639.
Laszlovsky et al., "Dopamine 02/03 Receptor Occupancy of RGH-188, a 03/02 Antagonist/Partial Agonist Antipsychotic, in Healthy Volunteers," 20th Congress of the European College of Neuropsychopharmacology, Vienna Austria, Oct. 13-17, 2007 , 1 page.
Laszy et al., "Dopamine D3 receptor antagonists improve the learning performance in memory impaired rats," Psychopharmacol., 179(3):567-575, (2005).
Layzer, "Degenerative Diseases of the Nervous System," Cecil Textbook of Medicine, 20th Edition, vol. 2, pp. 2050-2057, (1996).
Le Foll et al., "Dopamine D3 receptor ligands for the treatment of tobacco dependence," Expert Opin Investig Drugs, 16(1):45-57, (2007).
Lehr et al., "Lectin-mediated drug delivery: The second generation of bioadhesives," Journal of Controlled Release, 2000, 65(1-2):19-29.
LeClerc et al., "Pharmacological therapies for autism spectrum disorder: a review," P. T., Jun. 2015, 40(6):389-397.
Lehman et al., "Practice guideline for the treatment of patients with schizophrenia, second edition," Am. J. Psychiatry, 161(2 Suppl):1-56, (2004).
Lenert et al., "Public preferences for health states with schizophrenia and a mapping function to estimate utilities from positive and negative symptom scale scores," Schizophr Res., 71(1):155-165, (Nov. 1, 2004).
Leucht et al, "Second-generation versus first-gerneration antipsychotic drugs for schizophrenia: a meta-analysis," Lancet, 2009, 373:31-41.
Levant and McCarson, "D(3) dopamine receptors in rat spinal cord: implications for sensory and motor function," Neurosci Lett., 303(1):9-12, (Apr. 2001).
Levant et al., "Dopamine $D_3$ receptor: relevance for the drug treatment of Parkinson's disease," CNS Drugs, 12:391-402, (1999).
Ludwig et al., "The use of mucoadhesive polymers in ocular drug delivery," Advanced Drug Delivery Reviews, 2005, 57(11):1595-1639.
Levant, "The D3 dopamine receptor: neurobiology and potential clinical relevance," Pharmacol. Rev., 49(3):231-252, (1997).

(56) References Cited

OTHER PUBLICATIONS

Lim et al., "Pharmacological rescue of Ras signaling, GluAl-dependent synaptic plasticity, and learning deficits in a fragile X model," Genes Dev., Feb. 2014, 28(3):273-289.

Mailman et al., "Third generation antipsychotic drugs: partial agonism or receptor functional selectivity?" Curr Pharm Des., 2010, 16(5):488-501.

Maj et al., "Effect of antidepressant drugs administered repeatedly on the dopamine D3 receptors in the rat brain," Eur. J. Pharmacol. 351:31-37, (1998).

Martineau et al., "Catecholaminergic metabolism and autism," Dev. Med. Child. Neurol., Aug. 1994, 36(8):688-697.

Mcbride et al., "Serotonergic Responsivity in Male Young Adults With Autistic Disorder," Results of a pilot study: Arch. Gen. Psychiatiy., Mar. 1989, 46(3):213-21.

Millan et al., "S33084, a novel, potent, selective, and competitive antagonist at dopamine D(3)-receptors: II. Functional and behavioral profile compared with GR218,231 and L741,626," J. Pharmacol. Exp. Ther., 293:1063-1073, (2000).

Millan et al., "The dopamine D3 receptor antagonist, (+)-S 14297, blocks the cataleptic properties of haloperidol in rats," Eur. J. Pharmacol., 321:R7-R9, (1997).

Montgomery and Asberg, "A new depression scale designed to be sensitive to change," Br. J. Psychiatiy, 134:382-389, (1979).

Morissette et al., "High-throughput crystallization: polymorphs, salts, co-crystals and solvates of pharmaceutical solids," Adv Drug Deliv Rev. 56(3):275-300, Feb. 2004.

Mueser and McGurk, "Schizophrenia," Lancet, 363:2063-2072, (2004).

Müller-Oerlinghausen et al., "Bipolar disorder," Lancet, 359(9302):241-247, (2002).

Muly et al., "Relationship between dose, drug levels, and D2 receptor occupancy for the atypical antipsychotics risperidone and paliperidone," J Pharmacol Exp Ther, Apr. 2012, 341(1):81-9.

Murphy et al., "Autism spectrum disorder in adults: diagnosis, management, and health services development." Neuropsychiatr Dis Treat, Jul. 2016, 12:1669-86.

Nassar et al., "Improving the decision-making process in structural modification of drug candidates: reducing toxicity," Drug Discov Today, 9(24):4055-1064, (Dec. 2004).

Nassar et al., "Improving the decision-making process in the structural modification of drug candidates: enhancing metabolic stability," Drug Discov Today., 9(23):1020-1028, (Dec. 2004).

Nemeth et al., "Cariprazine versus risperidone monotherapy for treatment of predominant negative symptoms in patients with schizophrenia: a randomised, double-blind, controlled trial," Lancet., 389:1103-1113, Mar. 18, 2017.

Nyberg et al., "Positron emission tomography of in-vivo binding characteristics of atypical antipsychotic drugs. Review of D2 and 5-HT2 receptor occupancy studies and clinical response," Br. J. Psychiatry, Suppl., 29:40-44, (1996).

Oblak et al., "Reduced serotonin receptor subtypes in a limbic and a neocortical region in autism," Autism Res., Dec. 2013, 6(6):571-583.

PCT International Preliminary Report on Patentability in International Appln. No. PCT/IB2018/054227, dated Dec. 17, 2019, 8 pages.

PCT International Search Report and Written Opinion in International Appln. No. PCT/IB2018/054227, dated Sep. 20, 2018, 12 pages.

Pacher and Kecskeméti, "Cardiovascular side effects of new antidepressants and antipsychotics: new drugs, old concerns?" Curr. Pharm. Des., 10(20):2463-2475, (2004).

Papp and Wieronska, "Antidepressant-like activity of amisulpride in two animal models of depression," J. Psychopharmacol., 1446-52, (2000).

PCT International Search Report and Written Opinion in International Appln. No. PCT/US2009/50835, dated Sep. 10, 2009, 8 pages.

PCT International Search Report in International Appln. No. PCT/HU04/00056, dated Nov. 11, 2004.

Penagarikano et al., "Absence of CNTNAP2 leads to epilepsy, neuronal migration abnormalities, and core autism-related deficits," Cell, Sep. 2011, 147(1):235-246.

Persico and Napolioni, "Autism genetics," Behav. Brain. Res., Aug. 2013, 251:95-112.

Pilla et al., "Selective inhibition of cocaine-seeking behaviour by a partial dopamine D3 receptor agonist," Nature, 400:371-375, (1999).

Posey et al., "Developing drugs for core social and communication impairment in autism." Child Adolesc. Psychiatr. Clin. N. Am., Oct. 2008, 17(4):787-801.

Preechagoon et al., "Improved Dissolution Rate of Poorly Soluble Drug by Incorporation of Buffers," Drug Development and Industrial Pharmacy., 2000, 26(8): 891-894.

Rabinowitz et al., "Negative symptoms in schizophrenia—the remarkable impact of inclusion definitions in clinical trials and their consequences," Schizophrenia Research, 2013, 150:334-338.

Reavill et al., "Pharmacological actions of a novel, high-affinity, and selective human dopamine D(3) receptor antagonist, SB-277011-A," J Pharmacol Exp Ther., 294(3):1154-1165, (Sep. 2000).

Rogóz et al., "Anxiolytic-like effect of nafadotride and PNU 99194A, dopamine D3 receptor antagonists in animal models," Pol J Pharmacol., 52(6):459-462, (2000).

Russell, "Neurobiology of animal models of attention-deficit hyperactivity disorder," J. Neurosci. Methods 161:185-198, (2007).

S. H. Kim, et al., "Preparation method of 4-biphenylacetic acid with high yield and high purity," Database WPI Week 200648, Thomson Scientific, London AN 206-468774, XP0-02581633, May 5, 2011.

Sachs, "Unmet clinical needs in bipolar disorder," J. Clin. Psychopharmacol., 2003, 23(3 Suppl 1):S2-S8.

Sautel et al., "Nafadotride, a potent preferential dopamine D3 receptor antagonist, activates locomotion in rodents," J. Pharmacol. Exp. Ther., 1995, 275:1239-1246.

Schneider and Przewlocki, "Behavioral alterations in rats prenatally exposed to valproic acid: animal model of autism," Neuropsychopharmacology, Jan. 2005, 30(1):80-89.

Schwartz et al., "Dopamine D3 receptor: basic and clinical aspects," Clin. Neuropharmacol., 1993, 16(4):295-314.

Schwartz et al., "Possible implications of the dopamine D(3) receptor in schizophrenia and in antipsychotic drug actions," Brain Res. Rev., Mar. 2000, 31(2-3):277-287.

Seeman, "Dopamine D2 receptors as treatment targets in schizophrenia," Clin Schizophr Relat Psychoses., 4(1):56-73, (Apr. 2010).

Seeman, "Antipsychotic drugs, dopamine receptors and schizophrenia," Clin. Neurosci. Res., 1:53-60, (2001).

Seeman, "Brain dopamine receptors" Pharmacological Reviews, 32(3): 229-313 (1980).

Shafer and Levant, "The D3 dopamine receptor in cellular and organismal function," Psychopharmacology (Berl), v, 135:1-16, (1998).

Shahid et al., "Asenapine: a novel psychopharmacologic agent with a unique human receptor signature," J. Psychopharmacol., Jan. 2009, 23(1):65-73.

Shalev et al., "Neurobiology of relapse to heroin and cocaine seeking: a review.," Pharmacol. Rev. 54 (1), 1-42, (2002).

Shapiro et al., "Aripiprazole, a novel atypical antipsychotic drug with a unique and robust pharmacology," Neuropsychopharmacology, Aug. 2003, 28(8):1400-1411.

Sigala et al., "Opposite effects of dopamine $D_2$ and $D_3$ receptors on learning and memory in the rat," Eur. J. Pharmacol., 336:107-112, (1997).

Smith et al., "Maximizing response to first-line antipsychotics in schizophrenia: a review focused on finding from meta-analysis," Psychopharmacology, Feb. 2019, 236(2):545-549.

Smith et al., "The dopamine D3/D2 receptor agonist 7-OH-DPAT induces cognitive impairment in the marmoset," Pharmacol. Biochem. Behav., 63:201-211, (1999).

Sokoloff et al., "Molecular cloning and characterization of a novel dopamine receptor (D3) as a target for neuroleptics," Nature, 1990, 347(6289):146-151.

(56) References Cited

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227), (1999).

Stahl and Grady, "A critical review of atypical antipsychotic utilization: comparing monotherapy with polypharmacy and augmentation," Curr. Med. Chem., 11:313-327, (2004).

Stahl, Essential Psychopharmacology: Neuroscientific Basis and Practical Applications, 2nd ed., p. 409, Cambridge University Press, pp. 409-414, (2000).

Steiner et al., "D3 dopamine receptor-deficient mouse: evidence for reduced anxiety," Physiol Behav., 63(1):137-141, print 1998, (1997).

Stemp et al., "Design and synthesis of trans-N-[4-[2-(6-cyano-1,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," J. Med. Chem., 43(9):1878-1885, (2000).

Tada et al., "Combined treatment of quetiapine with haloperidol in animal models of antipsychotic effect and extrapyramidal side effects: comparison with risperidone and chlorpromazine," Psychopharmacology, 2004, 176(1):94-100.

Tador et al., "In vitro pharmacology of aripiprazole, its metabolite and experimental dopamine partial agonists at human dopamine D2 and D3 receptors," Eur. J. Pharmacol., Oct. 2011, 668(3):355-365.

Teng et al., "Reversal of social deficits by subchronic oxytocin in two autism mouse models," Neuropharmacology, Jun. 2016, 105:61-71.

Thanos et al., "The effects of two highly selective dopamine D3 receptor antagonists (SB-277011A and NGB-2904) on food self-administration in a rodent model of obesity," Pharmacol Biochem Behav. 89: 499-507, (2008).

Ukai et al., "Effects of the dopamine D3 receptor agonist, R(+)-7-hydroxy-N,N-di-n-propyl-2-aminotetralin, on memory processes in mice," Eur. J. Pharmacol., 1997, 324:147-151.

Ulrich, "Crystallization," Kirk-Othmer Encyclopedia of Chemical Technology, 2002, Chapter 4, 7 pages.

Vahia, "Diagnostic and statistical manual of mental disorders 5: A quick glance," Indian J. Psychiatry, Jul. 2013, 55(3):220-3.

Van Aerde et al., "In vitro evaluation of modified starches as matrices for sustained release dosage forms," International Journal of Pharmaceutics, Jul. 1988, 45:145-152.

Van der Kooij and Glennon, "Animal models concerning the role of dopamine in attention-deficit hyperactivity disorder," Neuroscience and Biobehavioral Reviews, 2007, 31: 597-618.

Vanderschuren and Trezza, "What the laboratory rat has taught us about social play behavior: role in behavioral development and neural mechanisms," Curr. Top Behav. Neurosci., 2013, 16:189-212.

Vippagunta et al., "Crystalline solids," Adv Drug Deliv Rev., 48(1):3-26, (May 16, 2001).

Waters et al., "Differential effects of dopamine D2 and D3 receptor antagonists in regard to dopamine release, in vivo receptor displacement and behavior," J. Neural. Transm. Gen. Sect., 98:39-55, (1994).

West, "Solid Solutions," Solid State Chemistry and Its Applications, Wiley, Chapter 10, pp. 358, pp. 365 (1988).

Willner et al., "Dopaminergic mechanism of antidepressant action in depressed patients," J. Affective Disorders 86: 37-45, (2005).

Wong and Van Tol, "Schizophrenia: from phenomenology to neurobiology," Neurosci. Biobehav. Rev., 27(3):269-306, (2003).

World Health Organization, The World Health Report 2001; Mental Health: New Understanding, New Hope, http://www.who.int/whr/2001/en/2001, 169 pages (2001).

Wustrow et al., "Aminopyrimidines with High Affinity for Both Serotonin and Dopamine Receptors," J. Med. Chem., 1998, 41:760-771.

Wyatt and Henter, "An economic evaluation of manic-depressive illness—1991," Soc. Psychiatry Psychiatr. Epidemiol., 30(5):213-219, (1995).

Youdim, "The path from anti Parkinson drug selegiline and rasagiline to multifunctional neuroprotective anti Alzheimer drugs ladostigil and m30," Curr Alzheimer Res., 2006, 3(5):541-550.

Young et al., "A rating scale for mania: reliability, validity and sensitivity," The British Journal of Psychiatry, 1978, 133:429-435.

Zink et al., "Combination of amisulpride and olanzapine in treatment-resistant schizophrenic psychoses," Eur. Psychiatry, 2004, 19:56-58.

Chen et al, "A New and Practical Synthesis of Cariprazine through the Facile Construction of 2-[trans-4-(3,3 Dimethylureido)cyclohexyl] acetic Acid," Synthesis, Jun. 2016, 48:18:A-G.

Greene's Protective Groups in Organic Synthesis, 4th edition, 2006, Chapter 5, 543-544.

March's Advanced Organic Chemistry, 6th edition, Wiley, 2007, Chapter 16, pp. 1427-1434.

PCT International Search Report in International Appln. No. PCT/IB2017/054094, dated Oct. 26, 2017, 7 pages.

Szekely et al, "Genotoxic Impurities in Pharmaceutical Manufacturing: Sources, Regulations, and Mitigation," Chemical Review, 2012, 48 pages.

Torisawa et al, "Progress in arylpiperazine synthesis by the catalytic amination reaction," Bioorganic and Medicinal Chemistry, 2002, 10:12:4023-4027.

INDUSTRIAL PROCESS FOR THE PREPARATION OF CARIPRAZINE

This application is a National Stage application under 35 U.S.C. § 371 of International Application No. PCT/IB2017/054094, having an International Filing Date of Jul. 7, 2017, which claims the benefit of Hungary Patent Application Serial Nos. P1700197, filed May 9, 2017 and P1600420, filed Jul. 8, 2016.

FIELD OF THE INVENTION

The present invention provides an industrial process for the preparation of trans-N-{4-[2-[4-(2,3-dichlorophenyl)-piperazin-1-yl]-ethyl]-cyclohexyl}-N',N'-dimethylurea having the formula (1), commonly known as cariprazine.

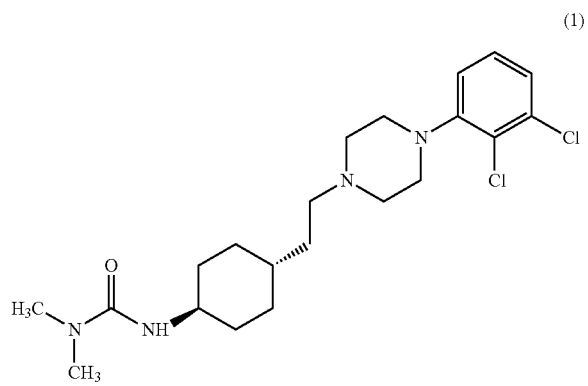 [SMILES: CN(C)C(=O)N[C@H]1CC[C@H](CCN2CCN(c3cccc(Cl)c3Cl)CC2)CC1]

TECHNICAL FIELD

The active agent dopamine D3/D2 receptor antagonist and its synthesis method was disclosed in the international patent application WO 2005/012266A1 first time. According to this process the base released from trans-N-{4-[2-[4-(2,3-dichlorophenyl)-piperazin-1-yl]-ethyl]-cyclohexyl}-N',N'-dimethylurea trihydrochloride is reacted with triphosgene. The targeted compound is received by crystallization of the product in methanol. Among others the disadvantages of this process include use of triphosgene for the development of isocyanate. Triphosgene, the compound itself is extremely toxic chemical compound and its use requires special arrangements under industrial conditions.

Trans-4-{2-[4-(2,3-dichlorophenyl)piperazin-1-yl]-ethyl}-cyclohexyl-amine trihydrochloride, the starting material of synthesis in accordance with the international patent application WO2005/012266A1, is produced by a well-known method disclosed in the international patent application WO2003/029233A1. Accordingly, 1-(2,3-dichlorophenyl)piperazine is coupled with trans-Boc-2-(4-aminocyclohexyl)acetaldehyde in a step of reductive amination, then from the intermediate compound the tert-butyloxycarbonyl protective group is cleaved with ethyl acetate in hydrochloric acid. Due to the chemical reaction carried out in dichloroethane realization of industrial scale process is hampered severely.

Trans-Boc-2-(4-aminocyclohexyl) acetic acid ethyl ester, the starting material for production of the aldehyde reagent is produced in the manner described in international patent application WO2010/070368A1. Accordingly, 4-nitrophenyl acetic acid is hydrogenated in the presence of palladium on carbon at 0.1-0.6 bar overpressure on temperature between 40° C. and 50° C., which is followed by "one pot" esterification to form trans-Boc-2-(4-aminocyclohexyl) acetic acid ethyl ester. Then from this reaction mixture trans-Boc-2-(4-aminocyclohexyl)acetaldehyde is obtained by partial reduction method described in the publication of Journal of Medicinal Chemistry, 2000, vol. 43, #9 p. 1878-1885. The main disadvantage of this reduction is that due to suppression of the excessive hydrogenation DIBALH reagent has to be added to the reaction mixture on −78° C., this temperature represents a difficult challenge to be met in most industrial plants.

The other reaction partner used in the coupling reaction mentioned above, the 1-(2,3-dichlorophenyl)-piperazine can be produced from piperazine and 1-bromo-2,3-dichlorobenzene with Buchwald reaction method according to the publication of Bioorganic and Medicinal Chemistry, 2002, vol. 10, #12 p. 4023-4027.

The 1-(2,3-dichlorophenyl)-piperazine is N-alkylated with 2-{trans-4-[(tert-butoxycarbonyl)amino]cyclohexyl}ethyl methanesulfonat in the manner disclosed in international patent application WO2010/070369. 2-{Trans-4-[(tert-butoxycarbonyl)amino]cyclohexyl}ethyl methanesulfonat is obtained from trans-Boc-2-(4-aminocyclohexyl)acetic acid ethylester by reduction which is followed by reaction with methanesulfonyl chloride. The disadvantage of the process is that methanesulfonate derivatives are remaining in the reaction mixture, which are considered potential genotoxic contamination, and detection of that can be difficult and the extent of this contamination should be kept at ppm level. Relevant information can be found for example on ACS Publications website at DOI: 10.1021/cr300095f. Chemical Reviews Gyorgy Szekely et al. Genotoxic Impurities in Pharmaceutical Manufacturing: Sources, Regulations, and Mitigation.

According to international patent application WO2015/056164 the protected derivative of trans-4-aminocyclohexyl acetic acid is reduced to alcohol with diisobutylaluminum hydride in tetrahydrofuran solution, which is followed by direct coupling of the obtained alcohol with 1-(2,3-dichlorophenyl)-piperazine. In the coupling reaction tri-ruthenium dodecacarbonyl complex formed with Xantophos is used. The downside of the procedure is the application of a costly catalyst and a ligand, in addition to that the cost-efficiency is reduced by chromatographic purification of the coupled product significantly.

A Chinese patent application having publication number of CN105330616A describes a method where cariprazine is produced with a process starting from ketone compound, namely from 4-(2-ethyl-hydroxyethyl)cyclohexanone. The first step in the production process is a Mitsunobu coupling reaction, to which diethyl azodicarboxylate is used. The reagent is known to be explosive, so this process cannot be scaled-up and it can be carried out in the industry with special preparations only. Afterwards, the resulting condensation intermediate can be converted into the corresponding cyclohexyl amine with hydroxylamine hydrochloride in the presence of benzyl amine or ammonia reducing reagent. Finally, the target compound is obtained by acylation with dimethyl-carbamoyl chloride. Moreover, the used starting compound 4-(2-hydroxyethyl) cyclohexanone is difficult to access, its production is a complicated process. During its production reagents and special protecting groups demanding unusual preparations can cause certain difficulties, which decreases the overall production efficiency.

According to the patent application US2001009912A1 in the first step 4-hydroxyphenyl-acetic acid ethyl ester is hydrogenated on 160° C. at 200 bar pressure for 72 hours, then the so obtained (4-hydroxycyclohexyl) acetic acid ethyl ester is oxidized with the extremely expensive Dess-Martin's periodate in order to produce (4-oxocyclohexyl) acetic acid ethylester.

According to the international patent application WO2006/44524A1 4-hydroxyphenylacetic acid ester is reduced with expensive rhodium catalyst. The starting material of the synthesis disclosed in Chinese patent application CN105330616A can be produced from ethyl-(4-oxo-cyclohexyl) acetate by introduction of different protecting groups only.

Taking into account all the listed solutions, we have set the goal of developing a new alternative cariprazine synthesis that is industrially feasible. The method can be accomplished through the synthesis of new intermediate compounds which have not been synthesized so far.

SUMMARY OF THE INVENTION

The invention provides a process for the preparation of cariprazine

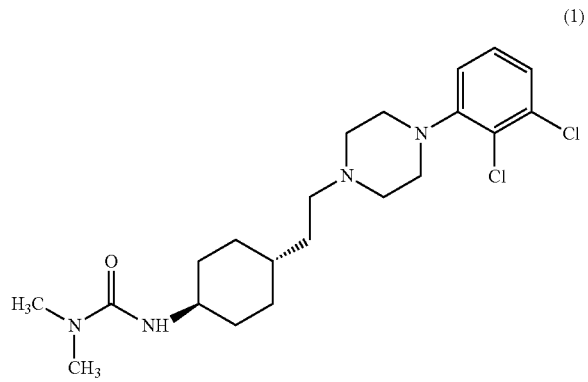 [SMILES: CN(C)C(=O)N[C@H]1CC[C@H](CCN2CCN(c3cccc(Cl)c3Cl)CC2)CC1]

(1)

wherein
  a) (trans-4-amino-cyclohexyl) acetic acid ethyl ester hydrochloride is converted to trans-4-aminocyclohexyl)-acetic acid or its hydrochloride by hydrolysis,
  b) from the obtained product with addition of dimethyl-carbamoyl derivative as a suitable reagent in presence of alkaline reagent (trans-4-{[(dimethylamino)carbonyl]amino}cyclohexyl) acetic acid is formed,
  c) then the obtained compound is linked to 1-(2,3-dichlorophenyl)-piperazine in the presence of carboxylic acid activating coupling reagent, and so 1,1-dimethyl-3-[trans-4-(2-oxo-2-(4-(2,3-dichlorophenyl)piperazin-1-yl-ethyl)cyclohexyl] urea is formed.
  d) which is converted to cariprazine borane adduct of formula (2).

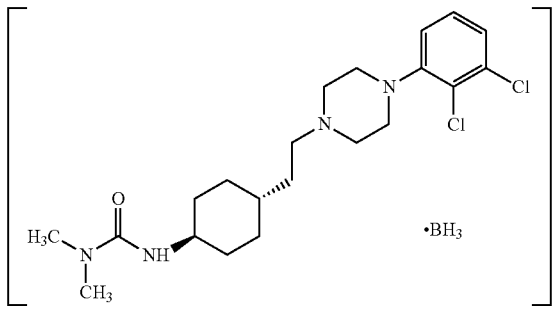

(2)

in the presence of reducing agent,
  e) and final product itself is eliminated directly or is obtained from its salt by a known method.

The invention also relates to a group of intermediate compounds that are formed and/or used in the process according to the present invention. These include (trans-4-{[(dimethylamino) carbonyl]amino}-cyclohexyl) acetic acid, 1,1-dimethyl-3-[trans-4-(2-oxo-2-(4-(2,3-dichlorophenyl)piperazin-1-ylethyl) cyclohexyl] urea and cariprazine borane adduct.

DETAILED DESCRIPTION OF THE INVENTION (Trans-4-aminocyclohexyl) acetic acid ethyl ester hydrochloride, the starting compound of the new process for preparation of cariprazine according to the present invention, is produced by the method disclosed in the international patent application WO2010/70368A1. This compound is converted into (trans-4-aminocyclohexyl) acetic acid or its hydrochloride by hydrolysis, from which by adding a suitable dimethyl-carbamoyl derivative in presence of alkaline reagent (trans-4 {[(dimethylamino)carbonyl]amino}cyclohexyl)-acetic acid is formed.

In order to form carboxylic acid (trans-4-aminocyclohexyl)-acetic acid ethyl ester hydrochloride is hydrolyzed under acidic or alkaline conditions by using reagents generally known from the literature, e. g. form Wuts, Peter G. M.: Greene's protective groups in organic synthesis—4th edition 543-544.

During the preparation of (trans-4{[(dimethylamino)carbonyl]amino}cyclohexyl)-acetic acid as a new chemical compound the amine group of (trans-4-aminocyclohexyl) acetic acid is reacted with a suitable halide, imidazolide, anhydride, or active ester of the dimethyl-carbamoyl acid, for example it is reacted with dimethyl-carbamoyl chloride in presence of an alkaline reagents such as sodium bicarbonate.

The obtained compound is linked to 1-(2,3-dichlorophenyl)-piperazine and so 1,1-dimethyl-3-[trans-4-(2-oxo-2-(4-(2,3-dichlorophenyl)piperazin-1-yl-ethyl)cyclohexyl] urea is provided. Only that kind of coupling reagents are suitable for the purpose of this chemical reaction, which are able to activate carboxylic acid and facilitate acylation of the secondary amino group of 1-(2,3-dichlorophenyl)-piperazine with trans-4-{[(dimethylamino)carbonyl]amino}cyclohexyl) acetic acid. These reagents, which can be also dehydrating agents, are reagents able to form an acid chloride from carboxylic acid such as thionyl chloride; agents capable to form reactive acyl-imidazolyl derivatives such as carbonyldiimidazole, carbodiimide; compounds such as N,N'-dicyclohexyl-carbodiimide and N,N'-diisopropyl-carbodiimide, that kind of benztriazole derivatives such as HATU, HBTU, HOBt or azabenzotriazoles such as PyAOP, PyBOP, HOAt are also can be used, and in addition to that boric acids, boronic acids, or the reagents that are well known by skilled persons in the art from chapters 16-72, 16-73 and 16-74 of the publication of Michael B. Smith and Jerry March having the title "March's Advanced Organic Chemistry" 6th edition Wiley in 2007 (Print ISBN: 9780471720911 Online ISBN: 9780470084960 DOI: 10.1002/0470084960) can be used as well. Optionally, 1,1-dimethyl-3-[trans-4-(2-oxo-2-(4-(2,3-dichlorophenyl)piperazin-1-ylethyl)cyclohexyl] urea that was formed at the end of the coupling reaction can be further processed in the next step.

The 1,1-dimethyl-3-[trans-4-(2-oxo-2-(4-(2,3-dichlorophenyl)piperazin-1-ylethyl)cyclohexyl]urea in the presence of reducing agent can be converted into the targeted compound. It is reacted with a reducing agent that is able to reduce amide functional group presented in the compound into a suitable amine while the urea functional group in the molecule structure remains unchanged under the conditions of the reaction, and so the targeted compound can be obtained. Suitable reducing agents include borans and their complexes, lithium aluminum hydride, lithium borohydride, triethylsilane and mixtures of the corresponding Lewis acids, or reagents which are listed in chapters from 19 to 64 of the aforementioned book (Print ISBN: 9780471720911 Online ISBN: 9780470084960 DOI: 10.1002/0470084960).

In comparison with processes described so far the advantage of the developed process is that utilization of protective group during the synthesis it is not necessary, and so the product manufacturing technology is simplified and the amount of materials used decreases accordingly, and in addition to that the emission of byproducts which are often classified as harmful substances to the environment is lower.

The Boc-trans-2-(4-aminocyclohexyl) acetic acid ethyl ester key intermediate compounds of the manufacturing processes disclosed in the international patent applications WO2003/029233, WO2010/070369 and WO2015/056164 has two protecting groups, namely the ester functional group and the Boc protecting group. For formation or removal of these functional groups separate chemical steps are required which are not necessary for the present invention. There is no need for reduction at low temperature; no solvents that prohibited in the industrial scale production are used; methanesulphonyl chloride is not used, which could form alkyl mesylate with alcohols, particularly methyl mesylate with methanol in the rest of the procedure. Additionally, catalysts (e.g.: $Ru_3(CO)_{12}$ catalyst) and ligands (e.g.: Xantphos) and method of preparative chromatography which all significantly increase the cost of the process are not used.

According to the process of the present invention during the hydrolysis of trans-4-aminocyclohexyl) acetic acid ethyl ester hydrochloride the starting material can be hydrolyzed both in acidic or basic medium. As a base alkali metal hydroxides, particularly sodium hydroxide can be used. Between 2 and 10 equivalent, optimally 2.5 equivalent amount of sodium hydroxide can be used. When acidic hydrolysis is carried out Brönsted acids, particularly hydrochloric acid is used for hydrolysis reaction. The concentration of the hydrochloric acid solution ranges from 2 mol/dm3 to 12 mol/dm3, optimally it is 6 mol/dm3. For both hydrolysis, water, a water miscible solvent, or a mixture of these are used throughout the reaction. In the case of a basic medium, this is mainly methanol-water, in case of acid hydrolysis water is used.

The term preparation of (trans-4-{[(dimethylamino)carbonyl]amino}cyclohexyl)-acetic acid refers to the reaction in which the (trans-4-aminocyclohexyl)-acetic acid is reacted with the corresponding halide, imidazolide, anhydride or an active ester of dimethylcarbamoyl acid, in the presence of bases, especially with dimethylcarbamoyl chloride. The amount of dimethylcarbamoyl chloride ranges from 1.0 equivalent to 2.0 equivalent, optimally 1.2 equivalent. Bases are referred to as Brönsted bases, mainly alkali metal carbonates and hydrogen carbonates, tertiary amines, optimally sodium bicarbonate. Acylation catalyst refers to pyridine or dimethylamino-pyridine. As reaction medium mainly water is used, but also hydrocarbons, ethers, esters and ketones, as well as their one-phase and two-phase mixtures with each other or with water can be used.

The 1-(2,3-dichlorophenyl)-piperazine compound is acylated with trans-4-{[(dimethylamino)carbonyl]amino}cyclohexyl) acetic acid. According to a preferred embodiment during the acylation the corresponding acid chloride is formed from carboxylic acid with thionyl chloride. According to another preferred embodiment the reaction is carried out "one pot" with the piperazine derivative, optionally in the presence of a base or acylation catalyst. 1-5 equivalent, optimally 2 equivalent amount of thionyl chloride is required for the formation of the acid chloride. Bases are referred to as Brönsted bases, mainly alkali metal carbonates and hydrogen carbonates, tertiary amines, preferably sodium bicarbonate or triethylamin. Acylation catalyst refers to pyridine or dimethylamino-pyridine. As reaction medium hydrocarbons, ethers, esters and ketones, as well as their one-phase and two-phase mixtures with each other or with water are used, but mainly toluene, acetone, dichloromethane, tetrahydrofuran can be used.

The acylation reaction step can be carried out also through acid-imidazolide. In this case, (trans-4-{[(dimethylamino) carbonyl]amino}cyclohexyl) acetic acid is dissolved in an appropriate solvent and carbonyl diimidazole is added to the solution. After the formation of the active intermediate 1-(2,3-dichlorophenyl)-piperazine compound is added to the reaction mixture. Finally, from the reaction mixture the desired 1,1-dimethyl-3-[trans-4-(2-oxo-2-(4-(2,3-dichlorophenyl)piperazin-1-ylethyl)cyclohexyl] urea is eliminated by crystallization. 1-5 equivalent, optimally 1-1.5 equivalent amount of carbonyl diimidazole may be used. As reaction medium hydrocarbons, ethers, esters and ketones, as well as their one-phase and two-phase mixtures, but mainly toluene, acetone, dichloromethane, tetrahydrofuran can be used. The reaction is carried out within the liquid range of the solvent, but optimally at a temperature between 20 and 25° C.

The obtained 1,1-dimethyl-3-[trans-4-(2-oxo-2-(4-(2,3-dichlorophenyl)piperazin-1-yl-ethyl) cyclohexyl] urea is reduced to Carprazine of formula (1). The reduction can be carried out with various types of borohydride compounds, among which the "alumina borohydride" produced in situ from sodium borohydride and aluminum chloride, have been found to be advantageous. In addition, several borane complexes reduce the acid amide to the corresponding amine, selectively. Borane complexes include complexes of borane ethers, optimally their complexes are formed with ether-type solvents. Borane complex refers to the complexes of boranes formed with Lewis bases, such as complexes formed with ethers, thioethers, amines, preferably complex formed with tetrahydrofuran.

Due to the difficult handling of borane, it is advantageously "in situ" formed with sodium borohydride or boron trifluoride etherate, iodine or Brönsted acids, preferably it is formed with boron trifluoride etherate. As a medium of reduction, ether type solvents are used, preferably the solvent may be tetrahydrofuran.

Surprisingly, we have found that after reduction of 1,1-dimethyl-3-[trans-4-(2-oxo-2-(4-(2,3-dichlorophenyl)piperazin-1-yl-ethyl)cyclohexyl] urea with borane reagents borane adduct of cariprazine was formed. By extracting the resulting compound, it has been found that in contrast to most of the Lewis base complexes of borane compounds, this product is not susceptible to moisture in the air, and it can be stored for several years without decomposition. It has been separable from both the starting acid amide and the targeted cariprazine product by thin layer chromatography. The intermediate can be isolated and then converted to cariprazine of formula (1).

For the hydrolysis of the intermediate, a suitable Brönsted acid solution can be used. Brönsted acids include organic and inorganic acids, mainly hydrochloric acid, sulfuric acid, phosphoric acid and acetic acid. The acid solvents used include one-phase and two-phase mixtures of hydrocarbons, ethers, esters and ketones with each other and/or with water, especially mixtures of acetone, methanol, ethanol, isopropanol and t-butanol with water. The intermediate can be thermally decomposed in a commonly used solvent.

The cariprazine salt, preferably a hydrochloride salt prepared according to the process of the present invention can be readily converted by skilled person into a cariprazine base by a simple method known from the state of the art.

The present invention is illustrated by the following non-limiting examples. The structure of the reaction products within the examples was determined by using VNMRS-400 NMR device and by measuring with PANalytical X'Pert PRO MPD X-ray powder diffraction (XRPD) apparatus.

EXAMPLES

Example 1

Trans-4-aminocyclohexyl acetic acid 2.21 g of trans-4-aminocyclohexyl acetic acid ethyl ester hydrochloride, 10 ml of methanol and 5 ml of 6N sodium hydroxide solution were charged into a flask. After 2 hours, from the mixture methanol was evaporated in vacuum and then 3 ml solution of 6N hydrochloric acid was dropped to the residue at 0-5° C. temperature. After stirring the suspension for 30 minutes, the product was filtered off and dried under vacuum at 45° C. temperature to constant weight. Thus 0.50 g of product in a white powder form was obtained (yield: 32%; DSC: 259.59-292.07° C.).

$^1$H NMR (D$_2$O, 800 MHz): 3.13 (tt, J=12.0, 4.0 Hz, 1H), 2.08 (d, J=7.4 Hz, 2H), 2.03 (br d, J=12.1 Hz, 2H), 1.81 (br d, J=12.9 Hz, 2H), 1.61-1.68 (m, 1H), 1.41 (qua d, J=12.5, 3.3 Hz, 2H), 1.09 (qua d, J=12.6, 3.0 Hz, 2H) ppm. $^{13}$C NMR (D$_2$O, 201 MHz): 185.5, 53.0, 47.5, 36.9, 33.1, 32.8 ppm. MS: ESI pos.: [M+H]$^+$=158; ESI MS/MS, CID=35%, m/z (rel. int. %): 141(100), 123 (6).

Example 2

Trans-4-aminocyclohexyl-acetic acid hydrochloride 22.2 g of trans-4-aminocyclohexyl-acetic acid ethyl ester hydrochloride and 45 ml of 6N hydrochloric acid solution were charged into a flask. The reaction mixture was refluxed for 16 hours, cooled to 20-25° C. temperature and after 30 minutes stirring the product was filtered off from the resulting suspension, which was dried under vacuum at 45° C. temperature until constant weight. Thus 12.61 g of product is obtained in a white powder form (yield: 65%; DSC: 207.45-211.59° C.).

Example 3

Trans-4-{[(dimethylamino carbonyl]amino}cyclohexyl) acetic acid 33 ml of water and 1.90 g of trans-4-aminocyclohexyl-acetic acid hydrochloride were charged into a flask, then 3.36 g of sodium bicarbonate was added to the solution. The resulting solution was cooled to 0-5° C. temperature and 1.40 ml dimethyl-carbamoyl chloride was added to that dropwise. The reaction mixture was stirred for 30 minutes at this temperature and then for 2 hours at 20-25° C. The reaction mixture was cooled again to 0-5° C. and 7.5 ml of 6 N hydrochloric acid was added dropwise. After stirring for 30 minutes, the product was filtered off from the suspension and dried under vacuum at 45° C. temperatures to constant weight. Thus 2.03 g of a product was obtained in a white powder form (yield: 89%; DSC: 206.73-217.37° C.).

$^1$H NMR (DMSO-d$_6$, 500 MHz): 12.00 (br s, 1H), 5.86 (d, J=7.9 Hz, 1H), 3.32 (tt, J=11.7, 3.8 Hz, 1H), 2.75 (s, 6H), 2.09 (d, J=7.0 Hz, 2H), 1.65-1.78 (m, 4H), 1.50-1.61 (m, 1H), 1.20 (qua d, J=12.8, 2.6 Hz, 2H), 0.98 (qua d, J=12.6, 2.6 Hz, 2H) ppm. MS: EI pos.: M$^+$=228; m/z (rel. int. %): 228(27), 169(14), 156(18), 154(18), 127(28), 124(12), 96(19), 89(41), 88(26), 81(100), 80(39), 72(95), 60(53), 45(61), 44 (60).

Example 4

1,1-dimethyl-3-[trans-4-(2-oxo-2-(4-(2,3-dichloro-phenyl)piperazin-1-yl-ethyl)cyclohexyl]urea (via acid chloride)

To a round-bottomed flask under nitrogen gas 680 mg of trans-4-{[(dimethylamino)carbonyl]amino}cyclohexyl) acetic acid was dissolved in 3 ml of dichloromethane and to the solution 18 mg dimethylaminopyridine, then 0.7 ml thionyl chloride was added. After three hours, the reaction mixture was evaporated and the evaporation residue was added trough dropping funnel to a suspension of 620 mg of 1-(2,3-dichlorophenyl) piperazine in 4 ml of dichloromethane and 650 mg of sodium bicarbonate under continuous stirring. After the reaction was completed (TCL:DCM/MeOH=9:1), 11.0 ml of distilled water was added to the reaction mixture and then it was evaporated to 10.0 g weight under reduced pressure. To the residue 4.0 ml acetone was added, the precipitate was stirred at room temperature for 1 hour, filtered and washed with 0.6 ml of distilled water. It was dried in a vacuum to a constant weight at 45° C. temperature. Thus 0.85 g of product was obtained in a white powder form (yield: 64.4%; DSC: 190.54-195.75° C.).

Example 5

1,1-dimethyl-3-[trans-4-(2-oxo-2-(4-(2,3-dichloro-phenyl)piperazin-1-yl-ethyl)cyclohexyl]urea (via acid imidazolidone)

To a round-bottomed flask under nitrogen gas 3.40 g of trans-4-{[(dimethylamino) carbonyl]amino}cyclohexyl)-acetic acid in 20 ml acetone was solved and 2.90 g of carbonyldiimidazole was added to the solution. After 4 hours mixing, 2 ml of isopropanol was added and the mixture was stirred at room temperature for 40 minutes, followed by the addition of 2.1 ml of triethylamine and 3.45 g of 1-(2,3-dichlorophenyl)-piperazine. After stirring for an additional 18 hours at room temperature, 80 ml of distilled water was added. After stirring further for an hour, the precipitated material was filtered off and washed with 2×15 ml of distilled water. The product was dried in vacuum at 45° C. temperature to constant weight. Thus 5.37 g of product was obtained in a white powder form (yield: 94.4%).

$^1$H NMR (DMSO-d$_6$, 500 MHz): 7.30-7.34 (m, 2H), 7.12-7.17 (m, 1H), 5.85 (d, J=7.9 Hz, 1H), 3.59-3.65 (m, 4H), 3.29-3.39 (m, 1H), 2.89-2.99 (m, 4H), 2.75 (s, 6H), 2.24 (d, J=6.8 Hz, 2H), 1.69-1.78 (m, 4H), 1.58-1.68 (m, 1H), 1.16-1.6 (m, 2H), 0.95-1.05 (m, 2H) ppm. $^{13}$C NMR (DMSO-d$_6$, 126 MHz): 170.1, 157.6, 150.0, 132.7, 128.5, 126.4, 124.7, 119.9, 51.3, 51.0, 49.2, 45.4, 41.1, 39.1, 35.8, 33.9, 32.7, 31.7 ppm. MS: ESI pos.: [M+H]$^+$=441; ESI MS/MS, CID=35%, m/z (rel. int. %): 396(23), 353(100), 333(5), 231 (3).

Example 6

N'-[trans-4-[2-[4-(2,3-dichlorophenyl)-1-piperazinyl]ethyl]cyclohexyl]-N,N-dimethyl urea borane adduct To a flask used for sulphonation 2.64 g of 1,1-dimethyl-3-[trans-4-(2-oxo-2-(4-(2,3-dichlorophenyl)piperazin-1-yl-ethyl)cyclohexyl] urea, 16 ml of tetrahydrofuran and 0.51 g of sodium borohydride were charged, then to the resulting mixture temperature 1.63 ml of boron-trifluoride-diethyl etherate was added at 0-5° C. temperature. At the end of the addition, the mixture was stirred on a temperature between 0° C. and 5° C. for an additional hour, then the reaction mixture was warmed to room temperature and 64 ml of distilled water was added. The precipitated crystals were post-mixed for 1 hour, then filtered and washed with 2×4 ml of distilled water. It was dried in vacuum oven to constant weight at 50° C. temperature. Thus 2.46 g of product was obtained in a white powder form (yield: 92.8%; DSC: 151.51-157.78° C.).

$^1$H NMR (DMSO-$d_6$, 400 MHz): 7.36-7.30 (m, 2H), 7.15-7.21 (m, 1H), 6.53 (br s, 3H), 5.87 (d, J=7.9 Hz, 1H), 2.60-3.60 (br m, 11H), 2.75 (s, 6H), 1.68-1.81 (m, 4H), 1.44-1.57 (br m, 2H), 1.14-1.28 (m, 3H), 0.90-1.04 (m, 2H) ppm. MS: HRMS (ESI$^+$); [M+H]$^+$, calcd for $C_{21}H_{36}ON_4Cl_2B$: 441.23537; found: 441.23551. delta=0.31 ppm. ESI MS/MS, CID=35%, m/z (rel int %): 427(28), 396 (100).

Example 7

N'-[trans-4-[2-[4-(2,3-dichlorophenyl)-1-piperazinyl]ethyl]cyclohexyl]-N,N-dimethyl urea To a round-bottomed flask 100 mg of N'-[trans-4-[2-[4-(2,3-dichlorophenyl)-1-piperazinyl]ethyl]cyclohexyl]-N,N-dimethyl urea borane adduct was charged, then 2.0 ml of tertiary butanol was added and the resulting mixture was heated to reflux. When the reflux temperature was reached, a solution was formed, and crystallization was observed after 30 minutes. TLC was assayed for controlling of completion of the reaction, the suspension was cooled to 0-5° C. temperature and it was stirred for a further hour, then filtered and washed with 2×0.2 ml tertiary butanol. The product was dried in vacuum oven at 45° C. temperature until constant weight. The mass of the obtained white crystalline material was 90 mg (yield: 93%).

$^1$H NMR (DMSO-$d_6$, 400 MHz): δ 7.18-7.10 (m, 2H), 6.99-6.92 (m, 1H), 4.12 (d, J=7.5 Hz, 1H), 3.64-3.49 (m, 1H), 3.07 (br s, 4H), 2.88 (s, 6H), 2.63 (br s, 4H), 2.50-2.39 (m, 2H), 2.07-1.94 (m, 2H), 1.82-1.72 (m, 2H), 1.52-1.37 (m, 2H), 1.31-1.18 (m, 1H), 1.18-0.99 (m, 4H). $^{13}$C NMR δ 157.8 (C), 151.3 (C), 134.0 (C), 127.5 (C), 127.4 (CH), 124.5 (CH), 118.6 (CH), 56.7 (CH$_2$), 53.4 (CH$_2$), 51.3 (CH$_2$), 49.8 (CH), 36.1 (CH$_3$), 35.7 (CH), 34.0 (CH$_2$), 33.9 (CH$_2$), 32.1 (CH$_2$).

Example 8

N'-[trans-4-[2-[4-(2,3-dichlorophenyl)-1-piperazinyl]ethyl]cyclohexyl]-N,N-dimethyl urea borane adduct To a flask used for sulphonation 1.32 g of 1,1-dimethyl-3-[trans-4-(2-oxo-2-(4-(2,3-dichlorophenyl)piperazin-1-yl ethyl)cyclohexyl] urea, 8 ml tetrahydrofuran and 0.23 g sodium borohydride were measured, then, and while we were keeping the temperature between 0 and 5° C., to the resulting mixture a solution of 8 g of anhydrous aluminum chloride in 4.5 ml tetrahydrofuran was added. At the end of the addition, the mixture was stirred for a further hour at 0-5° C. temperature, then the reaction mixture was warmed to room temperature and after 4 hours of reaction, TLC was assayed for controlling of completion of the reaction. To the mixture 20 ml 2N hydrochloric acid solution was added at 0-5° C. temperature. The precipitated crystals were post-mixed for 1 hour, then filtered and washed with 2×2 ml of distilled water. The product was dried in vacuum oven at 50° C. until constant weight. Thus 1.10 g of product was obtained in a white powder form (yield: 83%)

DSC: 110.73° C. decomposition

Example 9

N'-[trans-4-[2-[4-(2,3-dichlorophenyl)-1-piperazinyl]ethyl]cyclohexyl]-N,N-dimethyl urea To a round-bottomed flask 100 mg of N'-[trans-4-[2-[4-(2,3-dichlorophenyl)-1-piperazinyl]ethyl]cyclohexyl]-N,N-dimethyl urea borane adduct was measured, then 2.0 ml of acetone was added and the reaction mixture was heated to reflux. After the reflux was reached, a solution was formed and thin layer chromatography was assayed for completion of the reaction after 24 hours, the suspension was cooled to 0-5° C. temperature, then it was mixed for an additional hour, filtered and washed with 2×0.2 ml of acetone. The product was dried in vacuum oven at 45° C. temperature until constant weight. The mass of the obtained white crystalline material was 70 mg (yield: 72%).

DSC: 201.78-209.41° C.

Example 10

N'-[trans-4-[2-[4-(2,3-dichlorophenyl)-1-piperazinyl]ethyl]cyclohexyl]-N,N-dimethyl urea To a round-bottomed flask 100 mg of N'-[trans-4-[2-[4-(2,3-dichlorophenyl)-1-piperazinyl]ethyl]cyclohexyl]-N,N-dimethyl urea borane adduct was measured, then 2.0 ml methyl isobutyl ketone was added and the reaction mixture was heated to reflux. After the reflux was reached, a solution was formed and after 15 minutes a thin layer chromatograph was assayed for completion of the reaction, the suspension was cooled to 0-5° C. temperature, then it was mixed further for one hour, filtered and washed with 2×0.2 ml of methyl isobutyl ketone. The product was dried in vacuum oven at 45° C. temperature until constant weight. The mass of the obtained white crystalline material was 70 mg (yield: 72%).

DSC: 200.91-208.88° C.

Example 11

N'-[trans-4-[2-[4-(2,3-dichlorophenyl)-1-piperazinyl]ethyl]cyclohexyl]-N,N-dimethyl urea To a round-bottomed flask 100 mg of N'-[trans-4-[2-[4-(2,3-dichlorophenyl)-1-piperazinyl]ethyl]cyclohexyl]-N,N-dimethyl urea borane adduct was measured, then a mixture of 1.9 ml dimethylacetamide and 0.1 ml of water was added. The suspension was heated to 45° C. temperature. Within one hour, the product was precipitated from the resulting solution. The suspension was cooled to 0-5° C. temperature, then it was mixed further for one hour, it was filtered and washed with 2×0.2 ml of water. The product was dried in vacuum oven at 45° C. temperature until constant weight. The mass of the obtained white crystalline material was 90 mg (yield: 93%).

DSC: 202.70-210.60° C.

Example 12

N'-[trans-4-[2-[4-(2,3-dichlorophenyl)-1-piperazinyl]ethyl]cyclohexyl]-N,N-dimethyl urea dihydrochloride To a round-bottomed flask 200 mg of N'-[trans-4-[2-[4-(2,3-dichlorophenyl)-1-piperazinyl]ethyl]cyclohexyl]-N,N-dimethyl urea borane adduct was measured, then 1.0 ml 6N hydrochloride solution was added and the mixture was heated to reflux. After the reflux was reached, 2.0 ml of distilled water was added, and the reaction mixture was cooled to 0-5° C. temperature, then it was mixed further for one hour, it was filtered and washed with 2×0.5 ml of water. The product was dried in vacuum oven at 45° C. temperature until constant weight. The mass of the obtained white crystalline material was 180 mg (yield: 79.4%). XRPD peaks ° 2θ (% Rel. Int.): 7.2 (8.7); 11.1 (14.4); 13.0 (40.2); 13.8 (47.0); 14.0 (30.1); 14.4 (41.4); 15.0 (86.3); 18.4 (100.0); 22.3 (37.9); 24.6 (70.5); 25.3 (58.6).

Example 13

N'-[trans-4-[2-[4-(2,3-dichlorophenyl)-1-piperazinyl]ethyl]cyclohexyl]-N,N-dimethyl urea hydrochloride To a round-bottomed flask 200 mg of N'-[trans-4-[2-[4-(2,3-dichlorophenyl)-1-piperazinyl]ethyl-cyclohexyl]-N,N-dimethyl urea dihydrochloride, 0.8 ml of methanol and 0.2 ml of 2N hydrochloric acid were measured. To the resulting solution 3.2 ml of distilled water was added dropwise over 20 minutes. The resulting slurry was stirred at 20-25° C., then it was filtered and washed with 2×50 ml of distilled water. The product was dried in vacuum oven at 45° C. temperature until constant weight. The mass of the obtained white crystalline material was 150 mg (yield: 81.0%).

XRPD peaks °2θ (% Rel. Int.): 6.6 (4.9); 7.3 (50.0); 13.2 (53.1); 14.3 (100.0); 14.6 (56.7); 16.9 (89.4); 21.1 (72.9); 22.4 (95.6); 24.8 (51.8); 26.5 (75.6); 26.8 (19.6).

Example 14

N'-[trans-4-[2-[4-(2,3-dichlorophenyl)-1-piperazinyl]ethyl]cyclohexyl]-N,N-dimethyl urea hydrochloride To a round-bottomed flask 400 mg of N'-[trans-4-[2-[4-(2,3-dichlorophenyl)-1-piperazinyl]ethyl]cyclohexyl]-N,N-dimethyl urea borane adduct was measured, then 0.3 ml of 6N hydrochloric acid, 0.1 ml of water and 1.6 ml of methanol were added. The reaction mixture was stirred at 60-65° C. temperature for 3 hours. The completion of the chemical reaction was checked, the reaction mixture was cooled and the methanol was evaporated in vacuum. The residue was taken up in 1.6 ml of distilled water, then it was stirred for 1 hour at room temperature and at 0-5° C. temperature for an additional hour, it was filtered and washed with 2×50 ml of distilled water.

The product was dried in vacuum oven at 45° C. temperature until constant weight. The mass of the obtained white crystalline material was 397 mg (yield: 94.4%).

XRPD peaks °2θ (% Rel. Int.): 6.6 (5.3); 7.3 (44.0); 13.1 (50.3); 14.2 (84.6); 14.6 (50.4); 16.9 (88.9); 21.1 (71.5); 22.4 (100.0); 24.8 (53.1); 26.5 (62.5); 26.8 (14.3).

Example 15

N'-[trans-4-[2-[4-(2,3-dichlorophenyl)-1-piperazinyl]ethyl]cyclohexyl]-N,N-dimethyl urea To a round-bottomed flask 1.00 g N'-[trans-4-[2-[4-(2,3-dichlorophenyl)-1-piperazinyl]ethyl]cyclohexyl]-N,N-dimethyl urea hydrochloride was measured, then 10 ml dichloromethane and 5 ml of saturated sodium bicarbonate solution was added. After stirring the reaction mixture for 15 minutes, the phases were separated and the aqueous phase was washed with 5 ml dichloromethane. The combined organic phase was dried and concentrated in vacuum. The 0.89 g of the evaporation residue was stirred in 6 ml of isopropyl alcohol for 15 minutes, filtered and washed with 2×1 ml of isopropyl alcohol. The product was dried in vacuum oven at 45° C. temperature until constant weight. The mass of the obtained white crystalline material was 0.83 g (yield: 90.0%).

DSC: 209.58-213.72° C.

The invention claimed is:

1. A process for the preparation of cariprazine

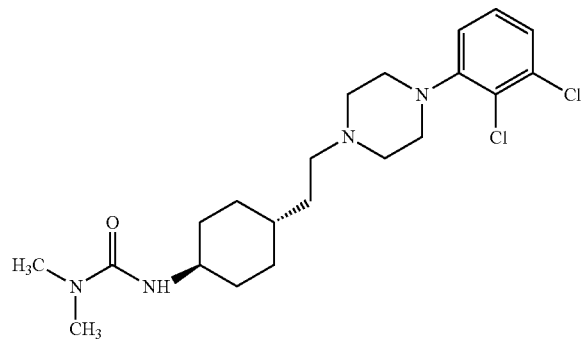

(1)

comprising:
a) converting (trans-4-amino-cyclohexyl)-acetic acid ethyl ester hydrochloride to (trans-4-aminocyclohexyl) acetic acid or its hydrochloride by hydrolysis,
b) adding a dimethylcarbamoyl derivative as a reagent to the (trans-4-aminocyclohexyl) acetic acid in the presence of an alkaline reagent to form (trans-4 {[(dimethylamino)carbonyl]amino}cyclohexyl) acetic acid,
c) linking (trans-4 {[(dimethylamino)carbonyl]amino}cyclohexyl) acetic acid to 1-(2,3-dichlorophenyl)-piperazine in the presence of a carboxylic acid activating coupling reagent to form 1,1-dimethyl-3-[trans- 4-(2-oxo-2-(4-(2,3-dichlorophenyl)piperazin-1-yl-ethyl)cyclohexyl] urea,
d) converting the 1,1-dimethyl-3-[trans- 4-(2-oxo-2-(4-(2,3-dichlorophenyl)piperazin-1-yl-ethyl)cyclohexyl] urea to the cariprazine borane adduct of formula (2),

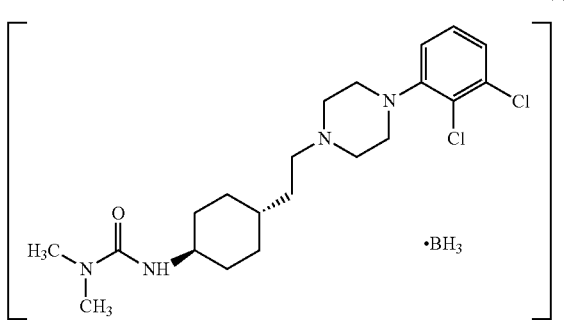

in the presence of a reducing agent, and e) obtaining the cariprazine by elimination or from a cariprazine salt.

2. The process according to claim 1 characterized by carrying out the hydrolysis of (trans-4-amino-cyclohexyl)-acetic acid ethyl ester hydrochloride by basic or acidic hydrolysis.

3. The process according to claim 1 characterized in that (trans-4-{[{dimethylamino)carbonyl]amino}cyclohexyl)-acetic acid is formed with dimethyl-carbamoyl chloride as the reagent.

4. The process according to claim 1 characterized in that the carboxylic acid activating coupling reagent is a dehydrating agent.

5. The process according to claim 1 characterized in that the carboxylic acid activating coupling reagent is carbonyldiimidazole or thionyl chloride.

6. The process according to claim 1 characterized in that the reducing agent is formed in situ from a suitable precursor.

7. The process according to claim 1 characterized in that the reducing agent is a borohydride having a cationic counter ion, a borane, or a complex thereof.

8. The process according to claim 7 characterized in that the borane complex is a complex of borane formed with a Lewis base.

9. The process according to claim 7 characterized in that the cationic counter ion is a positive ion of a metallic element.

10. The process according to claim 1 characterized in that after formation of the cariprazine borane adduct, a cariprazine salt is obtained by decomposition of the cariprazine borane adduct with a Brönsted acid in conventional solvents.

11. The process according to claim 10 characterized in that the Brönsted acid used for decomposition in conventional solvents is hydrogen chloride and the cariprazine salt obtained is cariprazine hydrochloride.

12. The process according to claim 11 characterized in that the cariprazine hydrochloride salt is converted into cariprazine.

13. The process according to claim 1 characterized in that the cariprazine borane adduct is thermally decomposed in conventional solvents to form cariprazine.

14. 1,1-Dimethyl-3-[trans-4-(2-oxo-2-(4-(2,3-dichlorophenyl)piperazin-1-ylethyl)cyclohexyl] urea cariprazine borane adduct of formula (2)

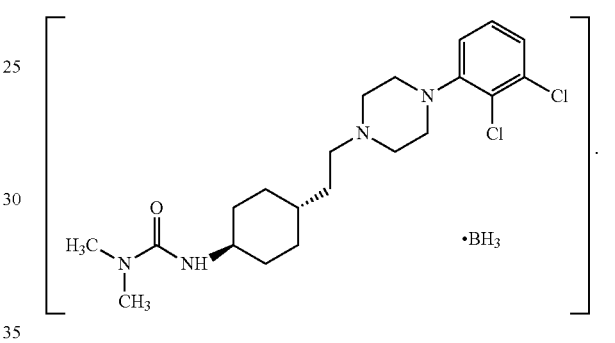

15. The process according to claim 8 characterized in that the borane complex is an ether, a thioether, an amine, or a tetrahydrofuran complex.

16. The process according to claim 9 characterized in that the cationic counter ion is an alkali metal, an alkaline earth metal, an earth metal, or aluminum.

* * * * *

UNITED STATES PATENT AND TRADEMARK OFFICE
CERTIFICATE OF CORRECTION

PATENT NO. : 11,274,087 B2
APPLICATION NO. : 16/316312
DATED : March 15, 2022
INVENTOR(S) : József Neu, Sándor Garadnay and Tamás Szabó

It is certified that error appears in the above-identified patent and that said Letters Patent is hereby corrected as shown below:

On the Title Page

Column 1, after Assignee, Line 1, delete "Nyrt." and insert -- Nyrt., Budapest (HU) --.

Column 1, after Foreign Application Priority Data, Line 2, below "Jul. 8, 2016 (HU) ................. 1600420" insert -- May 9, 2017 (HU) .................. 1700197 --.

Column 2, after Abstract, Line 3, delete "trans-" and insert -- (trans- --.

Column 2, after Abstract, Line 8, delete "1-{2,3-dichlorophenyl)~piperazine" and insert -- 1-(2,3-dichlorophenyl)-piperazine --.

Column 2, after Abstract, Line 11, delete "piperazin-1-yl-ethyl)" and insert -- piperazin-1-yl)ethyl) --.

In the Claims

Column 12, Approximately Line 56-57, in Claim 1, delete "(trans-4 {[(dimethylamino)carbonyl]" and insert -- (trans-4-{[(dimethylamino)carbonyl] --.

Column 12, Approximately Line 58, in Claim 1, delete "(trans-4 {[(dimethylamino)carbonyl]" and insert -- (trans-4-{[(dimethylamino)carbonyl] --.

Column 12, Line 63-64, in Claim 1, delete "[trans- 4-(2-oxo-2-(4-(2,3-dichlorophenyl)piperazin-1-yl-ethyl)cyclohexyl] urea" and insert -- [trans-4-(2-oxo-2-(4-(2,3-dichlorophenyl)piperazin-1-yl)ethyl)cyclohexyl]urea --.

Column 12, Line 65-66, in Claim 1, delete "[trans- 4-(2-oxo-2-(4-(2,3-dichlorophenyl)piperazin-1-yl-ethyl)cyclohexyl]urea" and insert -- [trans-4-(2-oxo-2-(4-(2,3-dichlorophenyl)piperazin-1-yl)ethyl)cyclohexyl]urea --.

Signed and Sealed this
Second Day of August, 2022

*Katherine Kelly Vidal*

Katherine Kelly Vidal
*Director of the United States Patent and Trademark Office*

Column 13, Line 25, in Claim 3, delete "(trans-4-{[{dimethylamino)" and insert -- (trans-4-{[(dimethylamino) --.

Column 14, Line 18, in Claim 14, delete "1-ylethyl)" and insert -- 1-yl)ethyl) --.